United States Patent [19]

Gewartowski

[11] 4,039,599
[45] Aug. 2, 1977

[54] XYLENE ISOMERIZATION PROCESS

[75] Inventor: Steve A. Gewartowski, Mount Prospect, Ill.

[73] Assignee: UOP Inc., Des Plaines, Ill.

[21] Appl. No.: 717,979

[22] Filed: Aug. 26, 1976

[51] Int. Cl.² ............................................. C07C 15/08
[52] U.S. Cl. .................................. 260/668 A; 203/28; 203/29; 203/71; 260/674 SA
[58] Field of Search .................... 260/668 A, 674 SA; 203/28, 71, 29

[56] References Cited

U.S. PATENT DOCUMENTS

| | | | |
|---|---|---|---|
| 2,640,804 | 6/1953 | Whitney | 203/29 |
| 2,892,001 | 6/1959 | Wallin | 260/674 SA |
| 2,899,474 | 8/1959 | Ricards | 260/674 SA |
| 3,078,318 | 2/1963 | Berger | 260/668 A |
| 3,553,276 | 1/1971 | Berger | 260/668 A |
| 3,624,172 | 11/1971 | Adams | 260/668 A |
| 3,626,020 | 12/1971 | Neuzil | 260/674 SA |
| 3,636,121 | 1/1972 | Stine et al. | 260/674 SA |
| 3,770,841 | 11/1973 | Meyers | 260/668 A |
| 3,773,846 | 11/1973 | Berger | 260/668 A |
| Re. 22,379 | 9/1943 | Dunn et al. | 203/71 |

Primary Examiner—Veronica O'Keefe
Attorney, Agent, or Firm—James R. Hoatson, Jr.; Robert W. Erickson; William H. Page, II

[57] ABSTRACT

A process for the production of paraxylene by the catalytic isomerization of xylenes wherein the reaction zone effluent is fractionated in three columns in series with the overhead product of the second column in the series being sent to a paraxylene separation zone, C₉ hydrocarbons being rejected as the bottoms product of the third column, and the overhead product of the third column being combined with the raffinate stream of the paraxylene separation zone and recycled to the isomerization zone.

4 Claims, 1 Drawing Figure

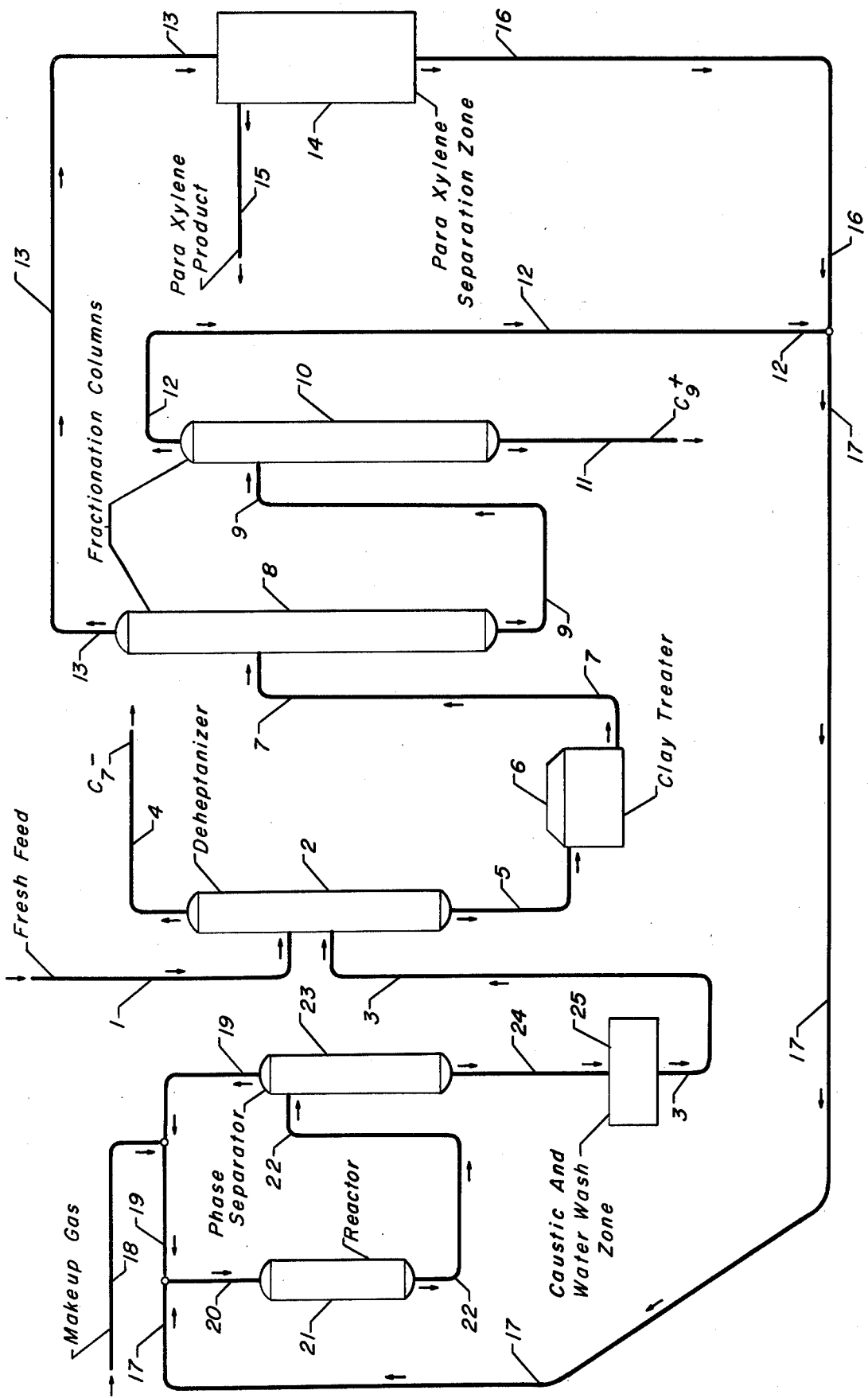

4,039,599

XYLENE ISOMERIZATION PROCESS

FIELD OF THE INVENTION

The invention relates to the field of mineral oil processing in general, and more specifically relates to a process for the isomerization of alkylaromatic hydrocarbons. Similar processes may be found in Class 260—668. The invention is particularly concerned with the method used to fractionate an isomerization zone effluent for the removal of hydrocarbons having nine or more carbon atoms per molecule.

PRIOR ART

The isomerization of alkylaromatics such as xylenes is a well established commercial process with which those skilled in the art are well acquainted. For instance, U.S. Pat. No. 3,078,318 (Cl. 260–668) describes a process for the production and recovery of a particular xylene isomer from a hydrocarbon mixture charged as a feed stream. This reference teaches an effective catalytic substance for use in the isomerization zone and describes in general terms the methods which may be used to separate the isomers. U.S. Pat. No. 3,553,276 presents an improvement in the fractionation performed upon the effluent of the xylene isomerization zone. This improvement comprises recycling toluene to the reaction zone and allowing the toluene to build up in the stream of naphthenes and unconverted xylene isomers. This allows the removal of the additional amounts of toluene which is formed in each pass through the isomerization zone by fractionation without the simultaneous removal of the majority of the naphthenes present in the recycle stream. This is beneficial to xylene production because undesired naphthenes are produced from xylenes in each pass of the recycle stream through the isomerization zone unless the naphthenes are present at their equilibrium concentration.

A description of the effects of various modes of operation of the xylene separation zone and of the requirement for $C_8$ naphthenes to be present in the isomerization zone is presented in the article appearing at page 173 of the September, 1973 edition of *Hydrocarbon Processing*. This reference is specifically directed to a combination process utilizing the isomerization zone and xylene separation zone systems and operating conditions which are preferred for use with the subject invention. The integration of these two zones for the production of specific isomers and a brief description of different commercial systems is presented in an article at page 48 of the November, 1967 issue of *The Oil and Gas Journal*.

This latter reference also indicates the method which has been heretofore used for the fractionation of the isomerization zone effluent prior to its passage into the xylene separation zone. Specifically, the effluent of the isomerization reactor is first cooled to effect the condensation of essentially all hydrocarbons except for normally gaseous hydrocarbons such as propane and methane. Phase separation of the partially condensed effluent produces a hydrogen-rich recycle stream which is recycled for admixture with the material being charged to the isomerization reactor and a liquid stream which is passed into a first fractionation column. This first column is a deheptanizer operated to remove toluene and other light ends overhead and to provide a bottoms stream comprising some toluene but mainly metaxylene, paraxylene, orthoxylene, naphthalenes and ethylbenzene. At this point the prior art resorts to superfractionation of the total deheptanizer bottoms stream in order to remove a very small amount of $C_9$-plus aromatics which are harmful to the molecular sieves used in the preferred xylene separation operation. By superfractionation is meant the use of a single fractionation column operated at a high reflux ratio and having the high number of theoretical trays necessary to produce a substantially pure bottoms stream of the undesirable heavy hydrocarbons and a $C_9$-plus free overhead. The second fractionation column may therefore have about 30 theoretical plates and utilize a reflux ratio of about 10:1 or higher. The overhead of the second column is directed to the xylene separation zone for recovery of the desired isomer. This is the prior art method which is used if it is desired to produce only paraxylene. If it is desired to simultaneously produce orthoxylene, then the desired amount of orthoxylene is removed in the bottoms product of the second fractionation column, and this bottoms product is passed into a third fractionation column referred to as an orthoxylene rerun column. These two fractionation methods are illustrated in U.S. Pat. Nos. 3,856,871, 3,856,872; 3,856,873 and 3,856,874 (all Cl. 260—688A) and 3,939,221 (Cl. 260—674).

The preferred molecular sieve xylene separation zone is known to those skilled in the art and is similar to that described in U.S. Pat. Nos. 3,201,491 (Cl. 260—676); 3,626,020 (Cl. 260-674SA) and 3,696,107. Specific examples of other molecular sieves and processes suitable for the separation of xylene isomers are described in U.S. Pat. Nos. 3,943,183 (Cl. 260—674SA) and 3,943,184.

SUMMARY OF THE INVENTION

The invention provides a combination xylene isomerization and separation process for the production of paraxylene which effects the rejection of $C_9$-plus aromatics and prevents these heavy aromatics from entering the separation zone without requiring superfractionation of the isomerization zone effluent. This is achieved by performing an imprecise separation in the second fractionation column to produce small bottoms stream containing both the objectionable heavy aromatics and some xylene isomers and then subjecting this bottom stream to further fractionation in a third column. The third fractionation column is also designed and operated to perform a rather imprecise separation. $C_9$-plus aromatics are removed as the bottoms product of this column and are also present in the overhead of the column. The overhead of the third column is recycled through the isomerization zone to build up the $C_9$-plus concentration in the feed to the third column. The subject process therefore eliminates the need for superfractionation of a relatively large stream by allowing the undesired components to buildup through recycling and then removing them at their rate of formation through adequate fractionation of a much smaller stream. The invention therefore differs from the prior art by the use of this unique fractionation system and by the provision of a recycle stream containing $C_9$-plus material which is returned to the isomerization zone.

Parenthetically, it should be observed that in the above cited references illustrating three fractionation columns and producing only paraxylene, such as U.S. Pat. No. 3,856,871, the first column is being used for the removal of ethylbenzene from the charge stock to the process and hence is not equivalent or pertinent to any column described in the appended claims. This ethylbenzene column is a feed prep column and does not act on the isomerization zone effluent.

DESCRIPTION OF THE DRAWING

The drawing presents a simplified illustration of the preferred embodiment.

Those skilled in the art will recognize that a great many subsystems such as valves, heat exchangers, reboilers and control systems have been omitted. It is contemplated that these accouterments will be used in the actual operation of the process. Those skilled in the art will also recognize that minor variations may be made to this flow scheme, such as the deletion of the caustic and water wash zone, without departing from the inventive concept.

A feed stream comprising all three xylene isomers, smaller amounts of ethylbenzene, toluene, $C_8$ naphthenes and paraffins, and also hydrocarbons having more than eight carbon atoms per molecule enters the process through line 1. The feed stream is passed into a deheptanizer 2 which produces an overhead stream removed in line 4. This overhead stream contains hydrocarbons having seven or less carbon atoms per molecule which entered the deheptanizer either through line 1 or in the isomerization zone effluent carried in line 3. The bottoms stream of the deheptanizer contains all hydrocarbons having eight or more carbon atoms per molecule and is removed in line 5. The deheptanizer bottoms stream is passed through a clay treating zone 6 for the polymerization of olefinic hydrocarbons and is then passed into a second fractionation column 8 through line 7. This column divides the incoming material into a second overhead product stream comprising the xylene isomers and ethylbenzene, and a second bottoms stream comprising orthoxylene, paraxylene and those hydrocarbons present which have more than eight carbon atoms. The second bottoms stream is passed into a third factionation column 10 through line 9. This rerun column produces a third bottoms stream comprising hydrocarbons having nine or more carbon atoms ($C_9$-plus hydrocarbons) which is removed in line 11. The overhead product stream of the third column is removed in line 12 and comprises orthoxylene, paraxylene and hydrocarbons having nine or more carbon atoms.

The second overhead product stream is passed through line 13 into a paraxylene separation zone 14 which produces a relatively pure stream of paraxylene by the use of molecular sieves. This paraxylene is removed as the product stream in line 15 and the remaining hydrocarbons are ejected as an effluent stream in line 16. This effluent stream is mixed with the second overhead product stream carried in line 12 to form a charge stream recycled to the isomerization zone in line 17. This charge stream is combined with a hydrogen-rich gas, including make-up hydrogen from line 18, which is carried in line 19. The resultant admixture enters line 20 and is heated by means not shown before being passed through an isomerization zone 21. The effluent of the isomerization reactor is cooled sufficiently to condense substantially all hydrocarbons having six or more carbon atoms by a cooling means not shown and is then passed into a vapor-liquid phase separator 23 via line 22. This separator produces the hydrogen-rich gas stream recycled in line 19 and a liquid-phase isomerization zone effluent stream transported in line 24. A caustic and water wash zone 25 is utilized to remove inorganic compounds injected into the reactor to promote high catalytic activity. The effluent of the wash zone is fed into the deheptanizer through line 3.

DETAILED DESCRIPTION

Processes for the production of paraxylene are of importance in the petroleum and petrochemical industries, with the paraxylene being used in the production of intermediates for synthetic fibers and plastics. Paraxylene is present to a limited extent in most unpurified petroleum fractions containing $C_8$ aromatic hydrocarbons, and it may be recovered from these streams. For instance, a reformate can be fractionated to produce a stream rich in $C_8$ aromatics and then this stream can be subjected to liquid extraction to remove paraffins and saturates. The remaining $C_8$ aromatics can then be separated through fractionation, crystallization or the use of molecular sieves to obtain specific xylene isomers. Flow schemes such as this fail to maximize paraxylene production, and other systems have therefore been developed which include an isomerization zone to increase the yield of specific isomers.

The subject process is specific to the production of paraxylene and does not effect the production of orthoxylene or metaxylene. This is accomplished through the use of a catalytic isomerization zone and a xylene separation zone which preferably contains a bed of molecular sieves. These two systems place various constraints on the manner in which the process is operated. For instance, as previously described it is desirable to retain naphthenes in the xylene stream which is recycled back to the isomerization zone in order to minimize the hydrogenation of xylenes to naphthenes. These naphthenes consist of various alkylcyclopentanes and alkylcyclohexanes such as 1,1,3-trimethylcyclopentane and 1,4-dimethylcyclohexane. A concentration of from about 3 to 12 mole percent, preferably from 5 to 10 mole percent, of naphthenes is therefore maintained in the feed to the isomerization zone.

Toluene is produced at a relatively constant rate in the isomerization zone by an irreversible reaction. It is therefore necessary to remove toluene at its rate of production, and this is one purpose of the deheptanizer. Toluene has a boiling point sufficiently below that of the $C_8$ aromatics to allow its easy separation from the aromatics by fractionation, but its boiling point is close enough to that of some naphthenes to make simultaneous rejection of the toluene and retention of the naphthenes difficult. The prior art has ameliorated this problem by recycling enough toluene to maintain about a 0.5 to 5.0 mole percent concentration in the feed to the isomerization zone.

The preferred xylene separation zone contains a bed of molecular sieves operated in accordance with U.S. Pat. No. 3,201,491 to simulate the use of a continuously moving bed of the molecular sieves. This includes the use of subsequent improvements to the process such as described in U.S. Pat. Nos. 3,696,107 and 3,626,020. The xylene separation zone is operated at adsorption conditions which include temperatures in the range of from about 30° to about 350° C., but preferably from 40° to 250° C. This zone may operate with either vapor phase or liquid phase process streams, with liquid phase operations being preferred. Pressures utilized may vary from atmospheric to about 1,000 psig., with more moderate pressures of from about 100 to 300 psig. being preferred. According to the preferred embodiment, the zone is operated with a vertical column of adsorbent to which the inlet and outlet positions of the feed stream, raffinate stream, extract stream and desorbent stream are periodically and unidirectionally shifted. These streams are then fractionated as necessary to remove contaminants introduced by these changes in inlet and outlet locations. This results in continuous process which produces a xylene product stream containing over 98% paraxylene. A more detailed description of this process is contained in an article entitled "The Parex Process for Recovering Paraxylene" which appeared at page 70 of *Chemical Engineering Process*, Volume 66, No. 9, September, 1970. The xylene separation zone may depart from this preferred embodiment through the use of batch-type operations or a true moving bed of molecular sieves. Other types of xylene separation zones using such operations as crystallization and fractionation are known and may be substituted.

As used herein the term molecular sieves is intended to refer to various natural and synthetic aluminosilicate adsorbents which exhibit an ability to preferentially adsorb selected xylene isomers. Preferred for use in the separation zone are synthetically prepared type X and type Y zeolites containing selected cations at the exchangeable cationic sites within the crystal structure. One suitable molecular sieve is a cation exchanged type X or type Y zeolite containing a single cation selected from potassium, barium, sodium and silver. A second suitable molecular sieve is a type X or type Y zeolite containing both a first cation chosen from the group consisting of potassium, rubidium, cesium, barium and silver, and a second cation selected from the group consisting of lithium, sodium, magnesium, calcium, strontium, beryllium, cadmium, cobalt, nickel, copper, manganese and zinc. These molecular sieves are described in greater detail in U.S. Pat. No. 3,626,020. Other adsorbents, including those not yet developed, can be used if they meet the criteria of adequate selectivity and longevity necessary for commercial operation. Two other adsorbents which are suitable for paraxylene separation are described in U.S. Pat. Nos. 3,943,183 and 3,943,184.

It has been found that exposure of the molecular sieves used in the xylene separation zone to $C_9$-plus aromatics results in degradation of the performance of the molecular sieve to a degree which cannot be tolerated. The prior art has therefore resorted to the superfractionation of the dehaptanized isomerization zone effluent in order to prevent the $C_9$-plus aromatics from entering the separation zone. In this mode of operation a bottoms stream comprising $C_9$-plus hydrocarbons and only a very small amount of $C_8$ aromatics is removed as the bottoms product of the superfractionator. All of the other deheptanized material is removed overhead, and the bottoms product is discarded. Any $C_8$ material in the superfractionator bottoms therefore reduces the yield of the overall process. This precise separation requires a very large fractionation column operating at a high reflux ratio and is therefore costly in terms of both capital costs and utilities. It is an objective of the subject invention to eliminate the need for performing this superfractionation while still preventing $C_9$-plus hydrocarbons from entering the xylene separation zone.

This objective is accomplished by charging the deheptanized isomerization zone effluent into a column which is operated and designed to produce an overhead stream free of the $C_9$ hydrocarbons and a small bottoms containing the $C_9$ hydrocarbons but also a sizable concentration of $C_8$ aromatics including orthoxylene. That is, a less precise fractionation of the deheptanized isomerization zone effluent is performed in the first column to which it is charged. Whereas the prior art attempted to limit the removal of $C_8$ aromatics in this second column in order to increase the xylene yield of the process, in the subject process at least 25 mole percent and preferably 50 mole percent of the subject bottoms stream is comprised of $C_8$ aromatic hydrocarbons. Operation in this manner produces a bottoms stream having a much higher concentration of $C_9$-plus hydrocarbons than the deheptanized isomerate stream and which may be adequately fractionated for the removal of the required amount of these hydrocarbons more readily than the larger deheptanized isomerate stream. The overhead stream of second fractionation column, commonly referred to as the xylene separation zone feed preparation column, is the feed stream to the xylene separation zone and comprises a mixture of all three xylene isomers. Since the three xylene isomers are relatively difficult to separate by fractionation, the $C_8$ hydrocarbons removed in the bottoms stream are likely to include all three xylene isomers. Exceptionally good fractionation could remove all paraxylene from the bottoms stream, but this is contrary to the objectives of the invention and is therefore not preferred. It is preferred that the flowrate, in moles per hour, of the overhead stream is from 10 to 50 times greater than the flowrate of the bottoms stream. The ratio of amounts of paraxylene, in moles per hour, in the overhead stream to the amount of paraxylene in the bottoms stream should exceed 20:1. Preferably, this ratio is in the range of from about 50:1 to about 200:1.

A second distinguishing feature of the subject process is the recycling of $C_9$-plus hydrocarbons through the isomerization zone in a manner similar to the prior art recycling of naphthenes and toluenes. This is performed as a second means of reducing the quality of the fractionation which must be performed to remove the $C_9$-plus hydrocarbons. Recycling some $C_9$-plus material allows its concentration to build up in the bottoms stream of the second column and eliminates the necessity of completely removing it from the overhead stream of the third fractionation column. The rate at which the $C_9$-plus material is recycled may exceed the rate at which it is removed. However, it is preferred that the amount of $C_9$-plus hydrocarbons which is recycled does not exceed the amount which is removed in the bottoms stream of the third fractionation column. Operation in this manner results in $C_9$ hydrocarbons being present in both the overhead and bottoms stream of the third fractionation column. This column is commonly referred to as the return column. It is operated in a manner effective to reject a fixed amount of $C_9$-plus material and to recover substantially all $C_8$ hydrocarbons in the bottoms stream of the second column. The rate of $C_9$ rejection is set to equal the sum of the amounts entering in the feed stream and formed in the process.

The paraxylene depleted raffinate stream of the separation zone and the overhead stream of the third frctionation column are combined and preferably vaporized before passage into the isomerization zone. Vaporiation is normally accomplished by admixture with a recycled hydrogen-rich stream and passage through a fired heater. It is preferred that the hydrocarbon feed stream to the process is not admixed with separation zone raffinate and passed directly into the isomerization zone since it will most likely contain an equilibrium concentration of paraxylene and this would reduce the production of paraxylene in the isomerization zone. The feed stream, which preferably contains all three xylene isomers, is therefore admixed with the isomerate prior to fractionation.

The isomerization zone may be of any type or configuration which is capable of effecting the catalytic isomerization of orthoxylene and metaxylene into paraxylene at commercially acceptable rates and conditions. Moving bed reactors, fixed bed reactors and fluidized reactors may all be used to perform the isomerization reaction. These reactors are subject to further variation in that the hydrocarbon reactants may be passed through the catalyst as a vapor or as a liquid, and in that the reactor may be operated with upward, downward or radial reactant flow.

The isomerization zone is operated at conditions effective to cause the isomerization of ortho and metaxylene to paraxylene. Besides the presence of a catalyst these conditions include a temperature of about 0° C. to about 600° C., preferably 320° C. to about 450° C., and a pressure of from about 1.0 to 100 atmospheres. Preferred is a pressure in the range of about 7 to 28 atmospheres and the use of a single fixed bed reactor operated with a downward flow of vapor phase reactants. The rate of hydrogen circulation should be sufficient to maintain a hydrogen to hydrocarbon mole ratio of from 1:1 to 20:1 in the reactor. This ratio is preferably kept within the range of about 1.5:1 to about 5:1. The amount of catalyst loaded in the reactor should provide a weight hourly space velocity (weight of hydrocarbons passing through the reactor in one hour per unit weight of catalyst) of about 0.5 to about 10 and preferably about 1 to 5. The exact conditions employed will normally vary with the age of the catalyst and are set by the activity of the catalyst and the effect of the conditions on selectivity, conversion and ultimate xylene yield of the isomerization zone.

Central to operation of the isomerization zone is an effective xylene isomerization catalyst. Several different suitable formulations are known to those skilled in the art and effective catalysts are available commercially. The catalyst will typically comprise an acidic inorganic oxide support such as alumina, silica-alumina mixtures, faujasites and mordenites which have been combined or impregnated with a metallic component. Preferred is an alumina based catalyst containing about 0.05 to about 5.0 wt. % of a Group VIII metallic component and 0.3 to 5.0 wt.% halogen. Particularly preferred is about 0.1 to about 1.5 wt.% of platinum or palladium and about 0.5 to 2.5 wt.% fluorine or about 0.1 to 1.5 wt.% chlorine. This halogen concentration may be maintained by the injection of halogen-containing substances such as carbontetrachloride into the material entering the isomerization zone. These catalytic composites may in addition contain from about 0.1 to about 1.0 wt.% sulfur to improve the performance. All percentages given in reference to catalyst composition are calculated on an elemental basis. Other catalysts which may be employed in the isomerization zone are described in some detail in U.S. Pat. Nos. 3,464,929; 3,409,685 and 3,409,686. The catalysts described in these references include an alumina matrix having less than 20 wt.% of finely divided mordenite dispersed in it and containing at least one metallic component chosen from nickel, platinum and palladium, about 0.001–2.0 wt.% sulfur and about 0.2 to 3.0 wt.% chlorine or fluorine. A second catalyst disclosed in these references has a base comprising an alumina matrix with less than 20 wt.% of finely divided mordenite dispersed in it and contains about 0.05 to 5.0 wt.% of platinum, or preferably palladium, and about 0.2 to 3.0 wt.% chlorine or fluorine. Other catalytic composites, including those not yet developed, may also be utilized.

The halogen content of the preferred catalysts result in the liquid phase isomerate having a halogen content which it is desirable to remove prior to fractionation. This is typically performed by sequential washing with caustic, an alkaline aqueous solution, to remove the halogens and with water to remove carried-over caustic. This operation is performed in liquid phase conditions at temperatures of from about 20° to about 200° C. and a pressure which is between that of the isomerization zone and the deheptanizer. Washing operations are well known to those skilled in the art and may be deleted if not made desirable by the catalyst system used.

The conditions employed in each of the three fractionation columns may vary over a relatively wide range, with the required temperatures being controlled by the pressure at which each individual column is operated. The properties of the materials fractionated in this process are well known, and the design of suitable columns and the selection of proper operating conditions are well within the capabilities of those skilled in the art. Representative overhead vapor temperature ranges are 110°–120° C. at about 30 psig. for the first column, about 155°–175° C. at about 10 psig. for the second column and about 160°–170° C. at about 150 psig. for the third column. Due to the increased cost of energy it is becoming a more common practice to operate the columns at a pressure of about 100 psig. or more and correspondingly high temperatures. This makes practical the use of heat removed in the overhead condenser of one column for reboiling a different column.

The feed stream to the process may contain a small amount of olefinic material. In addition, some olefins are normally produced in the isomerization zone. In order to remove these undesired impurities the bottoms stream from the deheptanizer is treated by passage as a liquid through a bed of suitable material. A proprietary clay such as Filtrol 24 supplied by the Filtrol Corporation is suitable for this purpose. This operation is carried out at a temperature of from 150° C. or lower to about 220° C. and a weight hourly space velocity of about 0.5 to 2.0. This clay is catalytically active and effects the oligomerization or polymerization of the olefins into relatively heavy hydrocarbons having more than eight carbon atoms and which are removed in the bottoms stream of the third fractionation column. A clay treater is normally operated at a pressure of about 5 to 150 psig. or as otherwise needed to maintain liquid phase conditions.

In accordance with the above description, the preferred embodiment of the invention is a process for the production of paraxylene from a feed stream comprising orthoxylene and metaxylene which comprises the steps of passing the feed stream into a first fractionation column operated under conditions effective to cause the separation of all hydrocarbons fed to the first fractionation column into a first overhead product stream comprising hydrocarbons having less than eight carbon atoms per molecule and a first bottoms stream comprising hydrocarbons having eight or more carbon atoms per molecule; passing the first bottoms stream into a second fractionation column which is operated at conditions effective to cause the separation of the first bottoms stream into a second overhead product stream comprising orthoxylene, metaxylene, paraxylene and ethylbenzene and a second bottoms stream comprising orthoxylene, metaxylene, paraxylene and hydrocarbons having more than eight carbon atoms per molecule; passing the second overhead product stream into a paraxylene separation zone comprising a bed of molecular sieves and operated at conditions effective to cause the formation of a relatively pure paraxylene product stream and a paraxylene separation zone effluent stream having a lower paraxylene concentration than said second overhead product stream; passing the second bottoms stream into a third fractionation column operated at conditions effective to separate the second bottoms stream into a third overhead product stream comprising hydrocarbons having more than eight carbon atoms per molecule, orthoxylene and paraxylene and a third bottoms stream comprising hydrocarbons having more than eight carbon atoms per molecule; admixing the third overhead product stream with the paraxylene separation zone effluent stream and effecting thereby the formation of a hydrocarbon charge stream; admixing a hydrogen stream with the hydrocarbon charge stream and passing the hydrocarbon charge stream through a catalytic xylene isomerization zone as a vapor while the xylene isomerization zone is maintained at conditions effective to cause the conversion of orthoxylene and metaxylene into paraxylene and effecting thereby the formation of an isomerization zone efluent stream; effecting a partial condensation of the isomerization zone effluent stream and passing the isomerization zone effluent stream into vapor-liquid separation zone which is operated at conditions effective to result in the separation of the isomerization zone effluent stream into the hydrogen stream and an isomerate stream; and, passing the isomerate stream into the first fractionation column. The invention may also be utilized with differing xylene separation methods if the presence of $C_9$ hydrocarbons is undesirable.

The invention is further illustrated by the following example based on conditions at the start of operations. The feed stream to the unit is about 6,890 lb/hr and comprises a relatively pure stream of $C_8$ hydrocarbons including ethylbenzene, orthoxylene, paraxylene and metaxylene and containing a total of about 0.5 mole percent of $C_7$ and $C_9$ hydrocarbons and a small amount of water. This stream is combined with the washed isomerate and passed into a 40-tray deheptanizer column operating with a bottoms liquid temperature of about 365° F. at a pressure of about 30 psig. About 21.5 mph (moles per hour) of material ranging from water and hydrogen to toluene and a very small amount of $C_8$ paraffins is removed overhead. A bottoms stream of about 401.3 mph is removed from the deheptanizer and passed into the second fractionation column. This stream contains about 9 mph of toluene and is clay treated at an inlet pressure of about 30 psig. and an inlet temperature of about 365° F.

The second column has 60 trays and is operated with a bottoms liquid temperature of about 355° F. at a pressure of about 18 psig. This column produces an overhead stream of about 389 mph which contains all entering hydrocarbons having seven or fewer carbon atoms and also the great majority of the ethylbenzene and xylenes. The 11.7 mph bottoms stream of the second column contains approximately 0.1 mph of ethylbenzene, 0.5 mph of paraxylene, 2.2 mph of metaxylene, 7.0 mph of orthoxylene and 1.9 mph of $C_9$ aromatic compounds. This bottoms stream is passed into a third fractionation column having 30 trays and operated with a bottom temperature of about 380° F. at 15 psig. This effects the separation of the entering material into a third bottoms stream containing about 1.4 mph of $C_9$ aromatic hydrocarbons and an overhead stream of about 10.2 mph. This overhead stream is combined with a stream of about 331.8 mph comprising the raffinate from the xylene separation zone. This forms the hydrocarbon stream which is charged to the isomerization zone after being mixed with a gas stream of about 3,409 mph. This gas stream includes gas recycled from the isomeriation zone and about 37 mph of makeup gas. The larger gas stream is about 60 mole percent hydrogen. The isomerization zone is a single reactor operated at an inlet pressure of about 200 psig. and inlet temperature of about 750° F. The effluent of this reactor is cooled to about 100°F. and passed into a vapor-liquid separator operated at about 150 psig. This produces the recycled gas and the liquid phase isomerate charged to the washing zone. The washing zone is operated at a temperature of about 100° F. and a pressure of about 150 psig.

The overhead of the second fractionation column is charged to a xylene separation zone of the preferred type and separated into the above described raffinate stream and an extract stream. Essentially all ethylbenzene entering in the feed stream is rejected in the xylene separation zone. The separation zone is operated at a pressure of about 125 psig. and a temperature of about 350 F. The extract stream has a flow rate of about 57.8 mph, of about 1.6 mph is toluene. The extract stream is then passed into a 60-tray finishing column operated at a bottoms liquid temperature of about 340° F. at 17 psig. The bottoms product of this column is a 55.8 mph paraxylene product stream having a purity above 99 mole percent. It is therefore evident that the invention provides a process which combines the known operations of xylene isomerization, fractionation and xylene separation in a new and useful manner which meets the objectives set out above.

I claim as my invention:

1. A process for the production of paraxylene which comprises the steps of:

a. passing an aromatic-rich feed stream into a first fractionation column operated under conditions effective to cause the separation of all hydrocarbons fed to the first fractionation column into a first overhead product stream comprising hydrocarbons having less than eight carbon atoms per molecule and a first bottoms stream comprising hydrocarbons having eight or more carbon atoms per molecule;

b. passing the first bottoms stream into a second fractionation column which is operated at conditions effective to cause the separation of the first bottoms stream into a second overhead product stream comprising orthoxylene, metaxylene, paraxylene and ethylbenzene and a second bottoms stream comprising orthoxylene, metaxylene, paraxylene and hydrocarbons having more than eight carbon atoms per molecule;

c. passing the second overhead product stream into a paraxylene separation zone operated at conditions effective to cause the formation of a relatively pure paraxylene product stream and a paraxylene separation zone effluent stream having a lower paraxylene concentration than said second overhead product stream;

d. passing the second bottoms stream into a third fractionation column operated at conditions effective to separate the second bottoms stream into a third overhead product stream comprising hydrocarbons having more than eight carbon atoms per molecule, orthoxylene and paraxylene and a third bottoms stream comprising hydrocarbon having more than eight carbon atoms per molecule;

e. admixing the third overhead product stream with the paraxylene separation zone effluent stream and effecting thereby the formation of a hydrocarbon charge stream;

f. admixing a hydrogen stream with the hydrocarbon charge stream and passing the hydrocarbon charge stream through a catalytic xylene isomerization zone as a vapor while the xylene isomerization zone is maintained at conditions effective to cause the conversion of orthoxylene and metxylene into paraxylene and effecting thereby the formation of an isomerization zone effluent stream;

g. effecting a partial condensation of the isomerization zone effluent stream and pasing the isomerization zone effluent stream into a vapor-liquid separation zone which is operated at conditions effective to result in the separation of the isomerization zone effluent stream into the hydrogen stream and an isomerate stream; and, h. passing the isomerate stream into the first fractionation column.

2. The process of claim 1 further characterized in that the flowrate of the second overhead product stream is over ten times greater than the flow rate of the second bottoms stream.

3. The process of claim 2 further characterized in that the ratio of the amount of paraxylene, in moles per hour, in the second overhead product stream to the amount of paraxylene in the second bottoms stream is greater than 20:1.

4. The process of claim 1 further characterized in that the paraxylene separation zone comprises a bed of molecular sieves.

* * * * *